(12) United States Patent
Lee et al.

(10) Patent No.: US 11,883,406 B2
(45) Date of Patent: Jan. 30, 2024

(54) METHOD FOR PRODUCING ALGINIC ACID-FOLIC ACID CONJUGATE, ALGINIC ACID-FOLIC ACID CONJUGATE PRODUCED THEREBY AND PHARMACEUTICAL COMPOSITION CONTAINING THE SAME

(71) Applicant: SEOUL NATIONAL UNIVERSITY R&DB FOUNDATION, Seoul (KR)

(72) Inventors: Kang Won Lee, Suwon-si (KR); Sa Ra Lee, Suwon-si (KR)

(73) Assignee: SEOUL NATIONAL UNIVERSITY R&DB FOUNDATION, Seoul (KR)

(*) Notice: Subject to any disclaimer, the term of this patent is extended or adjusted under 35 U.S.C. 154(b) by 53 days.

(21) Appl. No.: 17/590,217

(22) Filed: Feb. 1, 2022

(65) Prior Publication Data
US 2022/0241283 A1  Aug. 4, 2022

(30) Foreign Application Priority Data
Feb. 2, 2021 (KR) .................. 10-2021-0014488

(51) Int. Cl.
| | | |
|---|---|---|
| *A61K 31/519* | (2006.01) | |
| *A61K 47/61* | (2017.01) | |
| *A61P 35/00* | (2006.01) | |

(52) U.S. Cl.
CPC ............ *A61K 31/519* (2013.01); *A61K 47/61* (2017.08); *A61P 35/00* (2018.01)

(58) Field of Classification Search
CPC .... A61K 47/61; A61K 47/36; A61K 41/0061; A61K 49/0052; A61P 35/00
See application file for complete search history.

(56) References Cited

FOREIGN PATENT DOCUMENTS

| | | | | |
|---|---|---|---|---|
| CN | 103349783 A | * | 10/2013 | ............ C08B 37/10 |
| KR | 20180056308 A | | 5/2018 | |

OTHER PUBLICATIONS

Wang et al., Colloids and Surfaces B: Biointerfaces, 2015, 129, p. 63-70. (Year: 2015).*
Lee, Sara; "Study on Fluorescence Inducing pH-Sensitive Nanoparticle based on Folate Conjugated Alginate for Cancer Diagnosis"; Program in Nano Science and Technology, Graduate School of Convergence Science and Technology, Seoul National University; 4 pages.
The Polymer Society of Korea, Jun. 11, 2020, pp. 10-163.
Lee, Sa Ra et al., pH-Sensitive Folic Acid Conjugated Alginate Nanoparticle for Induction of Cancer-Specific Fluorescence Imaging, Oct. 6, 2020.

* cited by examiner

*Primary Examiner* — Jonathan S Lau
(74) *Attorney, Agent, or Firm* — DILWORTH IP, LLC

(57) ABSTRACT

The present invention relates to a method for producing an alginic acid-folic acid conjugate, an alginic acid-folic acid conjugate produced thereby, and a pharmaceutical composition containing the same. According to the method of producing an alginic acid-folic acid conjugate using a carboxy-protecting group and a leaving group, the hydroxyl group of alginic acid forms an ester group with the carboxyl group of folic acid. Thus, the alginic acid-folic acid conjugate may clearly distinguish cancer cells from normal tissue by more effectively targeting cancer cells than a conventional alginic acid-conjugated folic acid in which the amine group of folic acid is covalently bonded to the carboxyl group of alginic acid. Accordingly, the alginic acid-folic acid conjugate may be effectively used for precise diagnosis and efficient surgical resection of cancer lesions.

10 Claims, 12 Drawing Sheets

METHOD FOR PRODUCING ALGINIC ACID-FOLIC ACID CONJUGATE, ALGINIC ACID-FOLIC ACID CONJUGATE PRODUCED THEREBY AND PHARMACEUTICAL COMPOSITION CONTAINING THE SAME

BACKGROUND

1. Technical Field

This application claims the benefit of the filing date of Korean Patent Application No. 10-2021-0014488, filed with the Korean Intellectual Property Office on Feb. 2, 2021, the entire content of which is incorporated herein by reference. The present invention relates to a method for producing an alginic acid-folic acid conjugate, an alginic acid-folic acid conjugate produced thereby, and a pharmaceutical composition containing the same.

2. Related Art 5-aminolevulinic acid (5-ALA) has been used as a fluorescence inducing substance for tumor surgery since 1979 and is known to have few side effects when used clinically. When a patient takes 5-ALA, 5-ALA is converted to the intermediate protoporphyrin IX (PpIX) through mitochondrial heme biosynthesis in cancer cells. 5-ALA itself does not have fluorescence properties, but PpIX produced by the reaction of 5-ALA with cancer cells emits a fluorescence of 635 nm at an excitation wavelength of about 400 nm, making it possible to distinguish cancer cells from normal tissues.

However, most of contrast agents, including 5-ALA, which are used in optical diagnosis and surgery, are not specific to lesions, and hence accurate diagnosis or surgery is difficult. Thus, in order to impart lesion target specificity to the contrast agent, a method of crosslinking a tumor-specific ligand, such as a lesion-specific peptide, antibody or polysaccharide, to the contrast agent by covalent bonding has been actively used. However, when they are crosslinked by covalent bonding, new problems arise, such as decreases in the chemical structural stability and targetability of the complex, and side effects in the human body, which make it difficult to accurately diagnose cancer and achieve surgical resection.

In order to solve these problems, the present inventors have developed a drug carrier capable of targeting cancer cells without using covalent bonding with a tumor-specific ligand, that is, a micelle-structured nanocarrier including, as an inner phase, an aqueous phase component including a cancer cell fluorescence-inducing substance (such as 5-ALA) and a cancer cell targeting polysaccharide (Korean Patent No. 10-1901986). This nanocarrier may include, as the cancer cell targeting polysaccharide, a folic acid-conjugated alginic acid including alginic acid to which folic acid is conjugated so that it is capable of binding to folate receptors that are specifically overexpressed on the surfaces of cancer cells. However, the folate receptors on cancer cells recognize $NH_2$ of the dihydropteridine moiety of folic acid, and when folic acid-conjugated alginic acid is produced by a general production method, a problem arises in that the ability of the folic acid-conjugated alginic acid to bind to cancer cells is reduced because the amine group ($NH_2$) is linked to the carboxyl group (—COOH) of alginic acid.

Accordingly, the present inventors have developed a novel alginic acid-folic acid conjugate having increased cancer cell targeting efficiency due to exposure of the amine group of folic acid, and a method for producing the same.

PRIOR ART DOCUMENTS

Patent Documents (Patent Document 1) Korean Patent No. 10-1901986

SUMMARY

An object of the present invention is to provide a method of producing an alginic acid-folic acid conjugate using a carboxy-protecting group and a leaving group.

Another object of the present invention is to provide an alginic acid-folic acid conjugate in which the hydroxyl group of alginic acid is linked to the carboxyl group of folic acid, or a pharmaceutically acceptable salt thereof.

Still another object of the present invention is to provide a pharmaceutical composition for diagnosing cancer containing the alginic acid-folic acid conjugate or a pharmaceutically acceptable salt thereof.

However, the objects to be solved by the present invention are not limited to the above-mentioned problems, and other problems not mentioned herein will be clearly understood by those skilled in the art from the following description.

One aspect of the present invention provides a method for producing an alginic acid-folic acid conjugate including steps of: a) introducing a protecting group to the carboxyl group of alginic acid; b) introducing a leaving group to the carboxyl group of folic acid; and c) obtaining a reaction product between the alginic acid to which the protecting group has been introduced in step a) and the folic acid to which the leaving group has been introduced in step b).

The alginic acid is a natural anionic polysaccharide extracted from brown algae, and is a block copolymer composed of mannuronic acid and guluronic acid. Mammals including humans do not have an enzyme that degrades alginic acid, and thus the alginic acid can exist stably in the body, but is hydrolyzed through an acid catalyst in an acidic environment in lysosomes. The alginic acid contains a carboxyl group (—COOH) and a hydroxyl group (—OH).

In the present invention, in order to produce the alginic acid-folic acid conjugate, which is a cancer cell targeting polysaccharide, alginic acid may be used which does not have the ability to bind specifically to cancer cells, but has the advantages of being nontoxic, having excellent biocompatibility and biodegradability, and being inexpensive.

As used herein, the term "protecting group" refers to a functional group that is introduced to selectively block a specific reactive site so that a chemical reaction may occur selectively at other unprotected reactive sites.

The term "carboxy-protecting group" in the present invention refers to a functional group that protects the carboxyl group of alginic acid from unwanted reactions, and includes ester groups and heterocycloalkyl groups. Examples of such carboxy-protecting groups include, but are not limited to, substituted arylalkyl esters (e.g., esters with substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, etc.), alkyl or substituted alkyl esters (e.g., esters with methyl, ethyl, t-butyl allyl or t-amyl, triphenylmethyl, 4-methoxytrityl, 4,4'-dimethoxytrityl, 4,4',4"-trimethoxytrityl, 2-phenylprop-2-yl, etc.), thioesters (e.g., t-butyl thioester), silyl esters (e.g., esters with trimethylsilyl, t-butyldimethylsilyl, etc.), 1,3-oxazolinyl, and the like.

Specifically, the protecting group in step a) may be an unsubstituted or substituted benzyl group; trimethylsilyl, t-butyldimethylsilyl, or t-butyldiphenylsilyl; an unsubstituted or substituted alkyl group having 1 to 4 carbon atoms; or tetrabutylammonium. The substituent of the substituted benzyl group may be nitro, an alkyl group having 1 to 10 carbon atoms, or an alkoxy group having 1 to 10 carbon atoms. The substituent of the substituted alkyl group having 1 to 4 carbon atoms may be an alkyl group having 1 to 10 carbon atoms, an allyl group, a phenyl group, or an alkoxy group having 1 to 10 carbon atoms.

According to one embodiment of the present invention, the protecting group may be tetrabutylammonium (TBA). When tetrabutylammonium is introduced as the protecting group, it is possible to stably protect the carboxyl group of alginic acid until reaction with folic acid.

According to one embodiment of the present invention, step a) may be performed by introducing tetrabutylammonium to the carboxyl group of alginic acid by reacting tetrabutylammonium hydroxide (TBAOH) with the alginic acid.

Step a) may include producing alginic acid from alginic acid salt and introducing a protecting group to the carboxyl group of the alginic acid at a pH of 8 to 10. More specifically, alginate-TBA may be obtained by dissolving sodium alginate in a predetermined acidic solvent (HCl) to produce alginic acid and then allowing the alginic acid to react with TBAOH until pH 9 is reached.

For example, step a) may be represented by the following Reaction Scheme 1:

[Reaction Scheme 1]

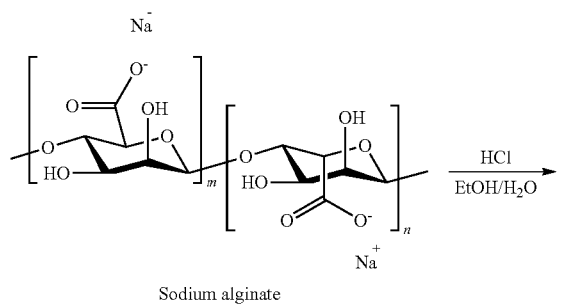

Sodium alginate

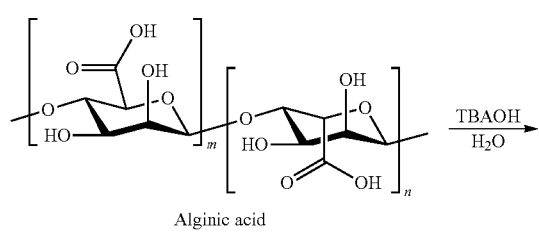

Alginic acid

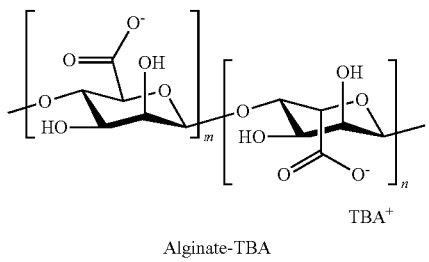

Alginate-TBA wherein m is an integer ranging from 10 to 60 (preferably 30 to 55), and n is an integer ranging from 10 to 60 (preferably 30 to 55).

Since the folic acid binds specifically to folate receptor-alpha, which is known to be overexpressed in the epithelium of cancer cells, it has been used as an agent for target drug delivery. It is known that the folate receptor-alpha is overexpressed in 90 to 95% of ovarian cancers. Such folic acid contains an amine group ($-NH_2$) and a carboxyl group.

In the present invention, folic acid, which has high affinity for folate receptor, non-immunogenicity, and stability, may be effectively used for targeting cancer cells, thereby promoting internalization of a nanocarrier containing the alginic acid-folic acid conjugate into cancer cells.

As used herein, the term "leaving group" refers to a functional group or atom that may be substituted by another functional group or atom in a substitution reaction.

The leaving group for the carboxyl group in the present invention is a functional group that binds to the carboxyl group of the glutamic acid moiety of folic acid and is substituted with the hydroxyl group of alginic acid upon reaction with the alginic acid. The leaving group for the carboxyl group may inhibit binding between the amine group of folic acid and the carboxyl group of alginic acid. Examples of the leaving group for the carboxyl group include, but are not limited to, an organosulfonyl group, an acyloxy group, an alkoxy group, an alkoxy carbonyl group (e.g., ethoxy carbonyl, etc.), halogens (e.g., iodine, bromine, chlorine, and fluorine), amido, azido, isocyanato, substituted or unsubstituted thiolate (e.g., thiomethyl, thiophenyl, etc.), and the like.

The leaving group in step b) is a methanesulfonyl group, a p-toluenesulfonyl group, or a trifluoromethanesulfonyl group; an alkoxy group having 1 to 5 carbon atoms; a halogen; or imidazole.

According to one embodiment of the present invention, the leaving group may be imidazole. When imidazole is introduced as the leaving group, the reaction of folic acid with alginic acid may be easily performed by effectively removing the leaving group upon the reaction. In this case, in order to introduce imidazole, which is a leaving group, to the folic acid, carbonyldiimidazole (CDI) may be used.

According to one embodiment of the present invention, step b) may be performed by introducing imidazole to the carboxyl group of folic acid by the reaction of CDI with folic acid, and may be represented by the following Reaction Scheme 2:

[Reaction Scheme 2]

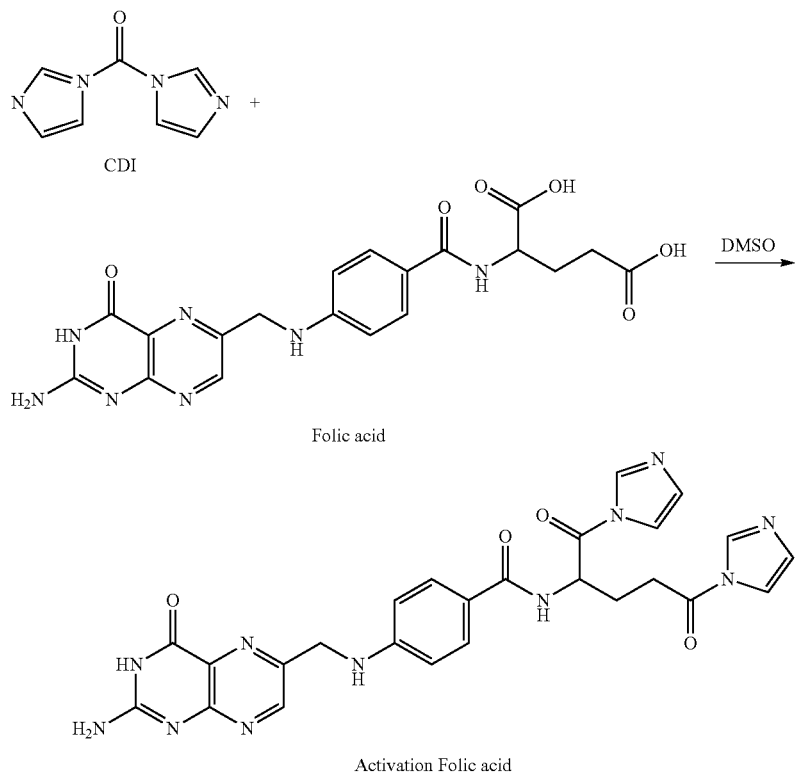

According to the reaction shown in Reaction Scheme 2 above, the leaving group may be introduced to the carboxylic acid of the glutamic acid moiety of folic acid, so that the reactivity thereof with the —OH group may increase.

More specifically, a folic acid (folic acid/CDI compound) containing a carboxyl group having increased reactivity may be obtained by dissolving folic acid in a predetermined solvent (e.g., DMSO), and then adding CDI thereto, followed by reaction for 12 to 28 hours under $N_2$ gas in a dark place.

According to one embodiment, the reaction product obtained in step c) may be one in which the hydroxyl group of alginic acid and the carboxyl group of folic acid are bonded to each other via an ester bond. For example, the synthesis of the alginic acid-folic acid conjugate may be achieved by forming an ester bond through a chemical reaction between the hydroxyl group of alginic acid having the carboxy-protecting group introduced thereto and the carboxyl group of folic acid having the leaving group introduced thereto, and may be represented by the following Reaction Scheme 3:

[Reaction Scheme 3]

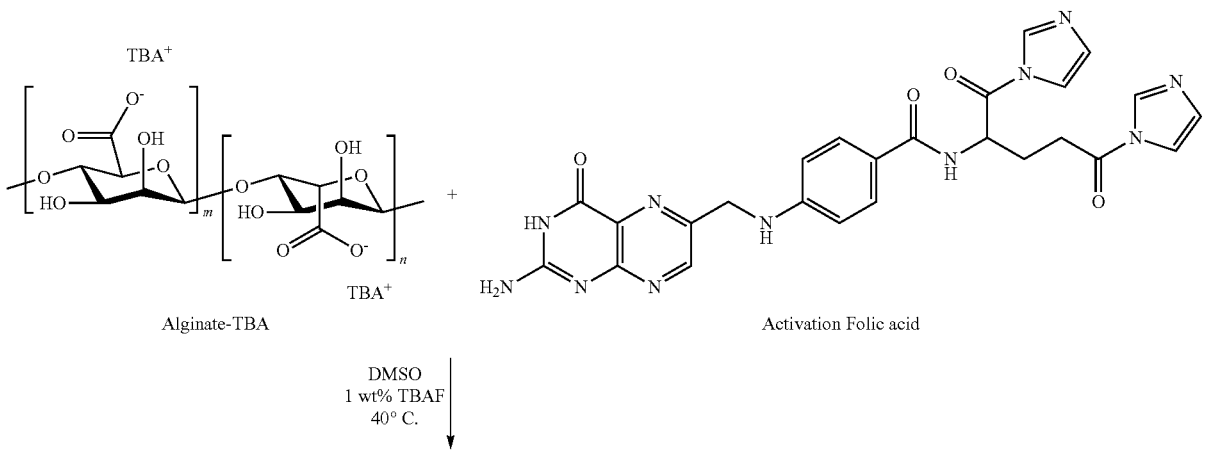

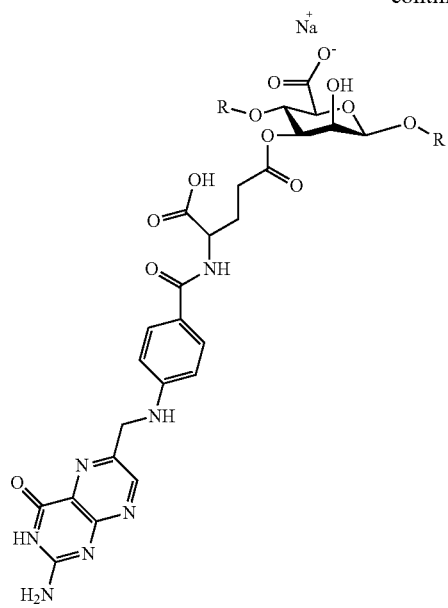

Alginate-Folic acid

More specifically, the alginic acid-folic acid conjugate may be obtained by dissolving alginate-TBA in a predetermined solvent (e.g., DMSO) containing 1 wt % TBAF, adding the activated folic acid/CDI compound to the solution, allowing the mixture to react for 4 to 18 hours in a dark place at 40° C. so as to form an ester bond between the alginic acid and the folic acid, and then performing a conventional process such as purification.

Another aspect of the present invention provides an alginic acid-folic acid conjugate in which the carboxyl group of folic acid is linked to the hydroxyl group of alginic acid via an ester bond, or a pharmaceutically acceptable salt thereof.

The amine group bound to the dihydropteridine moiety of the alginic acid-folic acid conjugate may remain unreacted. That is, the alginic acid-folic acid conjugate may be one in which the primary amine (—NH$_2$) group of the dihydropteridine moiety of folic acid may not form a bond with alginic acid.

The alginic acid-folic acid conjugate may be one in which the carboxyl group of the glutamic acid moiety of folic acid may form a bond with the hydroxyl group of alginic acid.

According to one embodiment of the present invention, the alginic acid-folic acid conjugate may be represented by the following Formula 1:

[Formula 1]

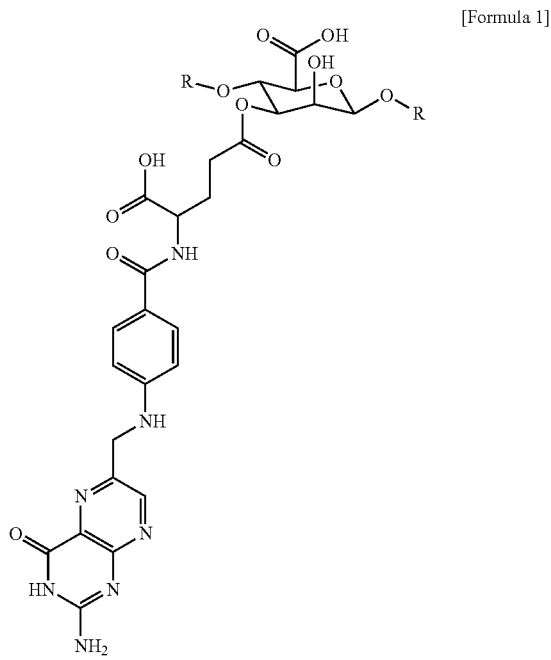

wherein R may be an alginic acid unit or an alginic acid polymer. When R in Formula 1 is an alginic acid polymer, it may be represented by the following Formula 2:

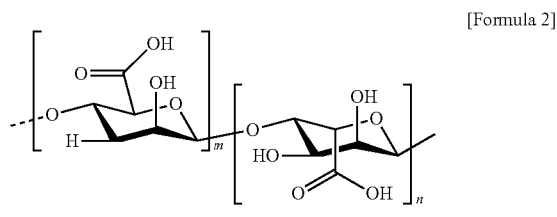

[Formula 2]

wherein m is an integer ranging from 10 to 60 (preferably 30 to 55), and n may be an integer ranging from 10 to 60 (preferably 30 to 55).

In the alginic acid-folic acid conjugate of Formula 1, the hydroxyl group of alginic acid forms an ester bond with the carboxyl group of folic acid so that the amine group of folic acid, which acts to bind to the folate receptor overexpressed by cancer cells, is exposed. Thus, the alginic acid-folic acid conjugate of Formula 1 may more effectively target cancer cells than a conventional alginic acid-conjugated folic acid in which the amine group of folic acid is covalently bonded to the carboxyl group of alginic acid.

According to one embodiment of the present invention, the salt of the alginic acid-folic acid conjugate may be represented by the following Formula 1-1:

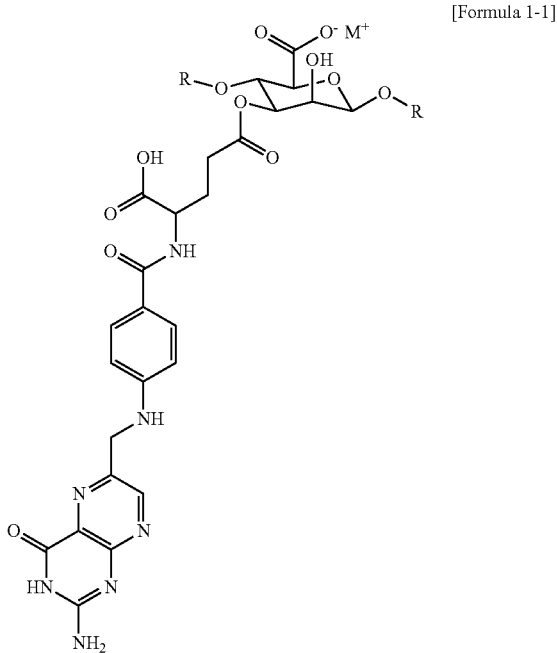

[Formula 1-1]

wherein R is an alginic acid unit or an alginic acid polymer, and M is Na, K, Mg, Ca, or Ba. In Formula 1-1 above, "M±" means a cation of an element, and includes a monovalent cation ($M^+$) of an element and a divalent cation ($M^{2+}$) of an element. In addition, R in Formula 1-1 may be the same as defined in Formula 1, and M in Formula 1-1 may be Na. That is, the salt of the alginic acid-folic acid conjugate may be represented by the following Formula 1-2:

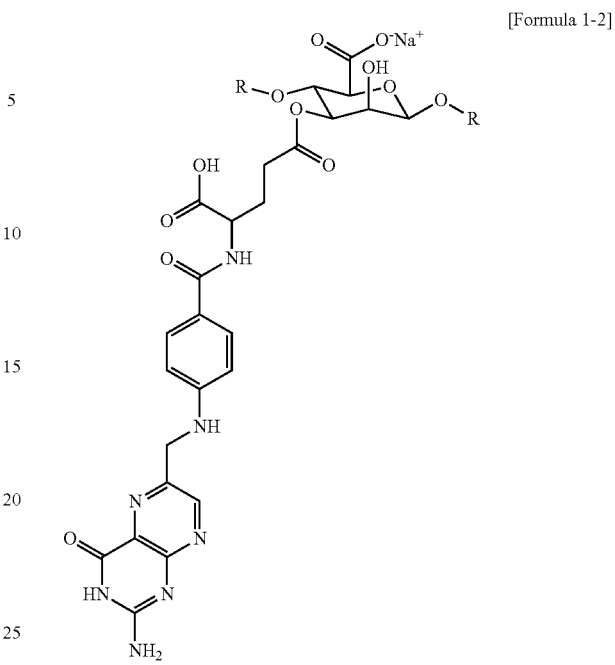

[Formula 1-2]

wherein R is the same as defined in Formula 1 above.

Still another aspect of the present invention provides a pharmaceutical composition for diagnosing cancer containing the alginic acid-folic acid conjugate or a pharmaceutically acceptable salt thereof.

According to one embodiment of the present invention, the pharmaceutical composition may further contain a cancer cell fluorescence-inducing substance.

As used herein, the term "cancer cell fluorescence-inducing substance" refers to any substance that may be internalized into cancer cells in vivo and generate a fluorescent substance. The cancer cell fluorescence-inducing substance may be any substance that is known in the art to be internalized into cancer cells to generate a fluorescent substance or that may be found in the future. For example, a substance that generates the fluorescent substance PpIX may be a cancer cell fluorescence-inducing substance selected from the group consisting of heme, hemin, zinc protoporphyrin, magnesium protoporphyrin, hematoporphyrin, benzoporphyrin, metalloporphyrin, 5-aminolevulinic acid, texaphyrins, chlorins, purpurins, bacteriochlorins, phthalocyanine, naphthalocyanine, and derivatives thereof, and any combination thereof, but is not limited thereto. The cancer cell fluorescence-inducing substance in the present invention is preferably 5-aminolevulinic acid (5-ALA).

According to one embodiment of the present invention, the pharmaceutical composition may contain a micelle-structured nanocarrier containing, as an inner phase, an aqueous phase component including the alginic acid-folic acid conjugate as a cancer cell targeting polysaccharide and the cancer cell fluorescence-inducing substance.

The nanocarrier may be obtained by mixing an oil phase component, a surfactant, and an aqueous phase component including the cancer cell fluorescence-inducing substance and the alginic acid-folic acid conjugate together to produce a water-in-oil (W/O) nanoemulsion, and then dispersing the nanoemulsion in water to remove the oil phase component, and may have a micelle structure including the aqueous phase component as an inner phase.

As used herein, the term "oil phase component" refers to a fat-soluble substance that is soluble in oil. As the oil phase component, any oil that may be used for the production of nanoemulsions in the art may be used without limitation. The term "aqueous phase component" refers to a water-soluble substance that is soluble in water. The aqueous phase component is an aqueous solution containing the cancer cell fluorescence-inducing substance and the alginic acid-folic acid conjugate in water as a medium.

According to one embodiment of the present invention, the micelle-structured nanocarrier including the alginic acid-folic acid conjugate and 5-ALA as the cancer cell fluorescence-inducing substance is an interpenetrating polymer network (IPN) nanoparticle. It was confirmed that the nanoparticle was not toxic to normal cells and cancer cells, selectively entered cancer cells (e.g., breast adenocarcinoma, lung cancer, ovarian adenocarcinoma, etc.) overexpressing folate receptor, generated PpIX in the cells, and emitted fluorescence at a wavelength of 405 nm (see FIG. 1).

According to one embodiment of the present invention, the nanocarrier may have the interpenetrating polymer network structure, and thus the alginic acid-folic acid conjugate and cancer cell fluorescence-inducing substance included in the aqueous phase component may be physically encapsulated, thereby increasing mechanical strength and thermodynamic stability. Furthermore, the nanocarrier may have a high absolute value of a zeta potential on the surface due to the cationic or anionic nature of the alginic acid-folic acid conjugate. Due to a repulsive force between the nanoparticles by such a high zeta potential, Ostwald ripening may be prevented, which makes it possible to increase the stability of the nanocarrier. In an experimental example, the change in the size of the nanocarrier produced according to one embodiment of the present invention was measured over time for 3 months using a dynamic light scattering analyzer while it was cold-stored, and as a result, it was confirmed that the diameter of the nanocarrier did not almost change, indicating that the nanocarrier is thermodynamically very stable.

According to one embodiment of the present invention, the nanocarrier may have an average particle size of about 200 nm or less, more specifically, 30 to 150 nm.

According to one embodiment of the present invention, the zeta potential of the nanocarrier may be −10 to −50 mV or 10 to 50 mV, more specifically, −10 to −30 mV or 10 to 30 mV. The zeta potential is a value obtained when the alginic acid-folic acid conjugate is negatively charged in the aqueous phase. The surface zeta potential value of the nanocarrier is changed by an ionic bond caused by an interaction between the substances encapsulated inside the nanocarrier. When the nanoparticle has a low zeta potential within the above range, a phenomenon such as Ostwald ripening may be prevented due to an increased repulsive force between the nanoparticles, and thus the nanoparticles may be maintained in a stable state.

According to one embodiment of the present invention, the nanoemulsion for producing the nanocarrier may contain, based on the total weight of the nanoemulsion, 70 to 80 wt % of the oil phase component, 10 to 20 wt % of the aqueous phase component, and 5 to 15 wt % of the surfactant.

When the nanoemulsion contain the components within the above-described ratio range, it is possible to control the size of the aqueous phase nanoparticle of the water-in-oil nanoemulsion, and to maintain the stability of the aqueous phase nanoparticle. Particularly, since the weight proportion of the aqueous phase component based on the total weight of the nanoemulsion is higher than the weight proportion of the surfactant, nano-sized particles may be formed and the stability of the particles is also excellent.

The nanocarrier according to the present invention may selectively deliver the cancer cell fluorescence-inducing substance to cancer cells rather than normal cells, and thus may be used as a pharmaceutical composition for diagnosing cancer, particularly a contrast agent, which clearly distinguishes cancer cells from normal tissue through fluorescence due to the fluorescent substance induced by the fluorescence-inducing substance internalized into cancer cells.

As used herein, the term "for diagnosing cancer" includes all of those used as a contrast agent to diagnose the presence of cancer as well as to monitor the treatment progress or the severity of cancer during cancer therapy. Furthermore, the term is meant to include the use of the contrast agent to clearly distinguish cancer tissue from normal tissue during surgical resection of the cancer tissue. In addition, the term is construed to include any beneficial application that may be obtained by distinguishing cancer tissue from normal tissue by fluorescence.

The cancer may be any cancer which may be targeted by the alginic acid-folic acid conjugate and where a fluorescent substance may be induced from the cancer cell fluorescence-inducing substance, and may vary depending on the specific kind of the cancer cell fluorescence-inducing substance and/or the alginic acid-folic acid conjugate. Examples of the cancer include, but are not limited to, brain tumor, lung cancer, stomach cancer, breast adenocarcinoma, and ovarian cancer.

The pharmaceutical composition for diagnosing cancer according to the present invention may be formulated in any dosage form capable of delivering the nanocarrier to cancer tissue for cancer diagnosis, and for example, may be formulated into an injectable formulation. When the composition is formulated into an injectable form, it may contain, as a diluent, a non-toxic buffer solution isotonic to blood, and for example, a phosphate buffer solution (pH 7.4) may be used. The pharmaceutical composition may contain other diluents or additives in addition to the buffer solution. The excipients and additives which may be added to this injectable formulation are widely known to those skilled in the art, and for these excipients and additives, reference may be made to, for example, the following literature: Remington's Pharmaceutical Sciences (19$^{th}$ ed., 1995); Dr. H. P. Fiedler "Lexikon der Hilfsstoffe fur Pharmazie, Kosmetik and angrenzende Gebiete" [Encyclopedia of auxiliaries for pharmacy, cosmetics and related fields].

The pharmaceutical composition is administered in a pharmaceutically effective amount. As used herein, the term "pharmaceutically effective amount" refers to an amount sufficient to treat a disease at a reasonable benefit/risk ratio applicable to any medical treatment. The effective dose level may be determined depending on factors, including the kind and severity of the patient's disease, the activity of the drug, sensitivity to the drug, the time of administration, the route of administration, excretion rate, the duration of treatment, and drugs used in combination with the composition, as well as other factors well known in the medical field. The composition according to one embodiment of the present invention may be administered individually or in combination with other therapeutic agents, and may be administered sequentially or simultaneously with conventional therapeutic agents. The pharmaceutical composition may be administered in a single or multiple dosage form. It is important to administer the pharmaceutical composition in the minimum amount that can exhibit the maximum effect without causing side effects, in view of all the above-described factors, and this amount can be easily determined by a person skilled in the art.

Specifically, the effective amount of the pharmaceutical composition according to one embodiment of the present invention may vary depending on the patient's age, sex and body weight. Generally, the active ingredient may be administered daily or every other day at a dose of 0.001 mg to 1,000 mg, 0.01 mg to 100 mg, or 0.1 mg to 10 mg per kg body weight, or may be administered 1 to 3 times a day at this dose. However, the dose is not intended to limit the scope of the present invention in any way, because the dose may increase or decrease depending on the route of administration, the severity of the disease, the patient's sex, weight and age, etc.

According to the method of producing an alginic acid-folic acid conjugate using a carboxy-protecting group and a leaving group according to the present invention, the hydroxyl group of alginic acid forms an ester bond with the carboxyl group of folic acid. Thus, the alginic acid-folic acid conjugate according to the present invention may clearly distinguish cancer cells from normal tissue by more effectively targeting cancer cells than a conventional alginic acid-conjugated folic acid in which the amine group of folic acid is covalently bonded to the carboxyl group of alginic acid. Accordingly, the alginic acid-folic acid conjugate according to the present invention may be effectively used for precise diagnosis and efficient surgical resection of cancer lesions.

The effects of the present invention are not limited to the above-described effects, and effects not mentioned herein will be clearly understood by those skilled in the art from the present specification and the accompanying drawings.

BRIEF DESCRIPTION OF THE DRAWINGS

FIG. 7(A) is a fluorescence image of HFBs which are normal cells, and FIGS. 7(B) and 7(C) are fluorescence images of MCF-7, A549 and SKOV-3, respectively, which are cancer cell lines. FIG. 7D is a bar graph of cell viability versus concentration of Np.

FIG. 9(A) is a fluorescence image of HFBs which are normal cells, and FIGS. 9(B), 9(C), and 9(D) are fluorescence images of A549, MCF-7 and SKOV-3, respectively, which are cancer cell lines. Cell nuclei are stained with DAPI and displayed in blue, and PpIX is displayed in red. Scale bar represents 50 μm.

DETAILED DESCRIPTION

Figure 1:
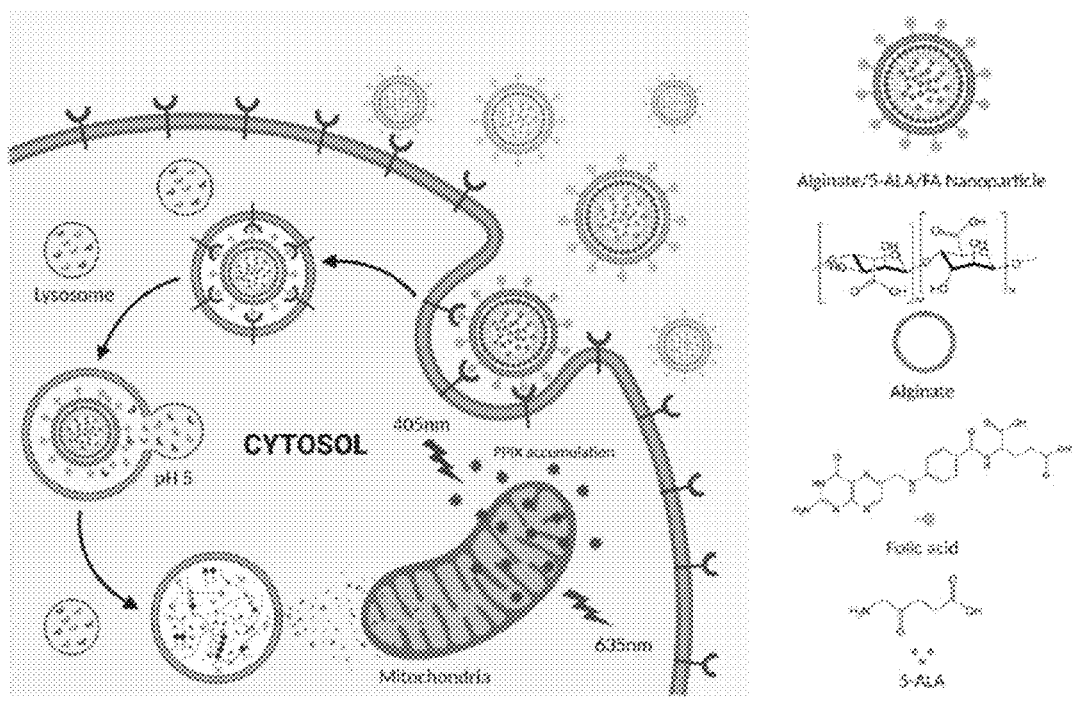
FIG. 1 illustrates that 5-ALA is delivered and released into cancer cells by a nanocarrier including an alginic acid-folic acid conjugate and 5-ALA according to one embodiment of the present invention.

Hereinafter, the present invention will be described in more detail with reference to examples. However, these examples are for illustrative purposes only to help the understanding of the present invention, and the scope of the present invention is not limited by these illustrative examples.

Example 1. Production of Nanocarrier Including Alginic Acid-Folic Acid Conjugate 1-1. Production of Alginic Acid-Folic Acid Conjugate To produce an alginic acid-folic acid conjugate (AF), sodium alginate (Wako Pure Chemical Industries, 11 kDa, Japan) (1 g, 4.632 mmol) was added to 30 mL of a mixture of ethanol/0.6 M HCl and stirred for 18 hours at 4° C. Alginic acid was produced, filtered in vacuo using qualitative filter paper (Whatmanm), washed several times with alcohol and acetone, transferred to a vial, and dried under vacuum overnight. The dried alginic acid was dissolved in water (30 mL) and 4% TBAOH (Sigma-Aldrich, USA) was added to the solution with continuous stirring until the solution reached pH 9. The opaque solution was lyophilized under reduced pressure to obtain white TBA-alginate (see Reaction Scheme 1).

Folic acid (Sigma-Aldrich, USA) (0.408 g, 0.9264 mmol) was mixed with DMSO (10 mL) and 1,10-carbonyldiimidazole (CDI) (Sigma-Aldrich, USA) (0.1502 g, 0.9264 mmol) was added thereto. The produced compound was stirred under $N_2$ gas at 25° C. in the dark for 24 hours (see Reaction Scheme 2).

Thereafter, TBA-alginate was dissolved in 50 mL of DMSO containing 1 wt % TBAF (tetrabutylammonium fluoride hydrate) (Sigma-Aldrich, USA). Under continuous stirring, the folic acid/CDI compound was added to the TBA-alginate solution and left to react overnight in the dark at 40° C. The product was precipitated in cold ethanol/methanol (1:1) containing 0.01 M HCl, filtered, and washed with alcohol. The product was neutralized by dissolving in a solution of sodium carbonate, and AF was obtained by lyophilization under reduced pressure (see Reaction Scheme 3 and Formula 1-2).

1-2. Production of Nanocarriers Containing Alginic Acid-Folic Acid Conjugate Nanocarriers (nanoparticles, NPs) containing AF were produced by referring to a conventional water-in-oil emulsion (W/O) preparation method (Jeong, Y. et al., *Biomacromolecules* 2019, 20, 1068-1076).

Briefly, soybean oil, a surfactant mixture (a mixture of Span80 and Tween80), and an aqueous phase component including AF and 5-ALA (98%) (Sigma-Aldrich, USA) were placed and mixed in a glass vial at a weight ratio of 7:2:1. For particle optimization, different nanocarriers (NPs) were prepared by adjusting the hydrophilic-lipophilic balance (HLB) values and AF concentration (0.5 to 1 wt %), while the concentration of 5-ALA was fixed at 1 wt %. The solution was mixed, followed by sonication without on-off pulse using a probe-type sonicator (VC-750, Sonics and Materials, USA) for 10 min at 40% amplitude. Then, the mixture was obtained as a yellowish opaque solution, which was redispersed in deionized (DI) water or phosphate-buffered saline (PBS) and centrifuged. The NPs collected in a liquid state were filtered using a syringe membrane filter (DISMIC-25, Advantec, Japan). Lastly, dialysis was performed for 24 hours using a dialysis membrane (Cellu-Sep MWCO 25 kDa) to remove impurities from the NP solution, thereby obtaining final NPs 1 to 4.

Comparative Example 1. Production of Nanocarrier Containing Alginic Acid

A nanocarrier containing an alginic acid was produced in the same manner as in Example 1, except that alginic acid was used instead of AF.

Figure 2:
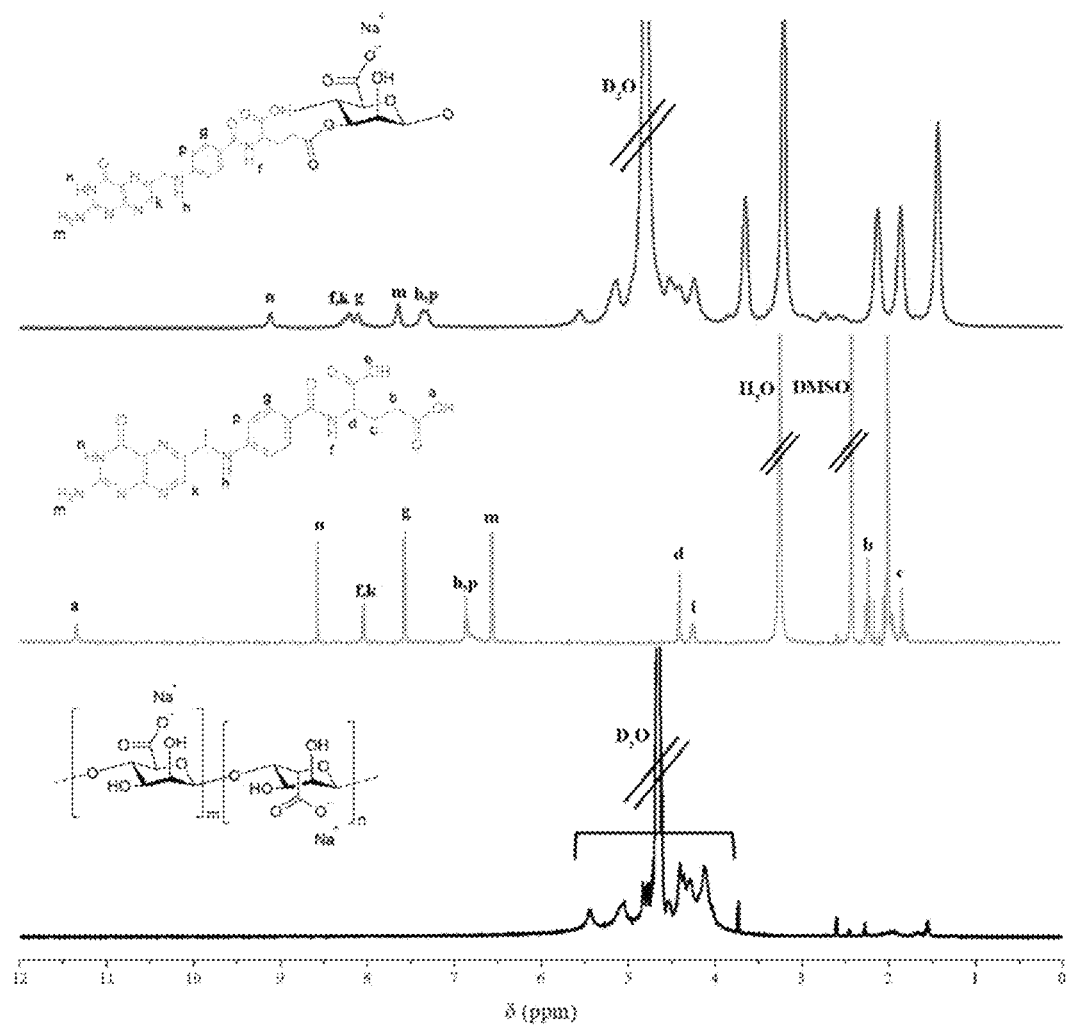
FIG. 2 shows the $^1$H NMR spectra of the alginic acid-folic acid conjugate according to one embodiment of the present invention, folic acid, and alginic acid.
Figure 3A:
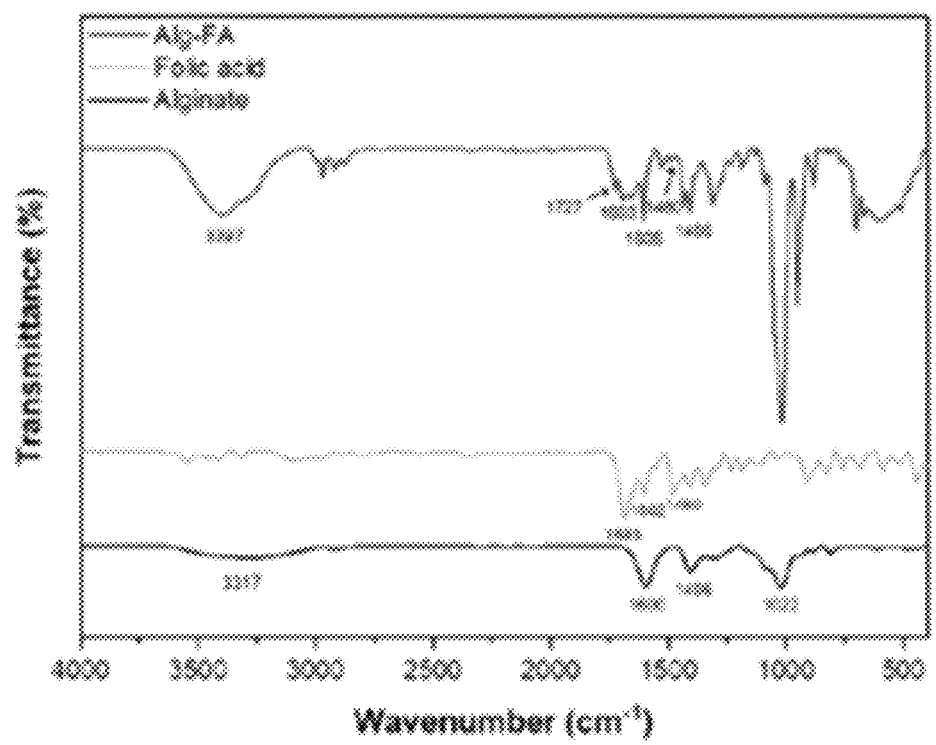
FIGS. 3A and 3B show FT-IR spectra (FIG. 3A) and UV-vis spectroscopy (FIG. 3B) of the alginic acid-folic acid conjugate according to one embodiment of the present invention, folic acid, and alginic acid.
Figure 3B:
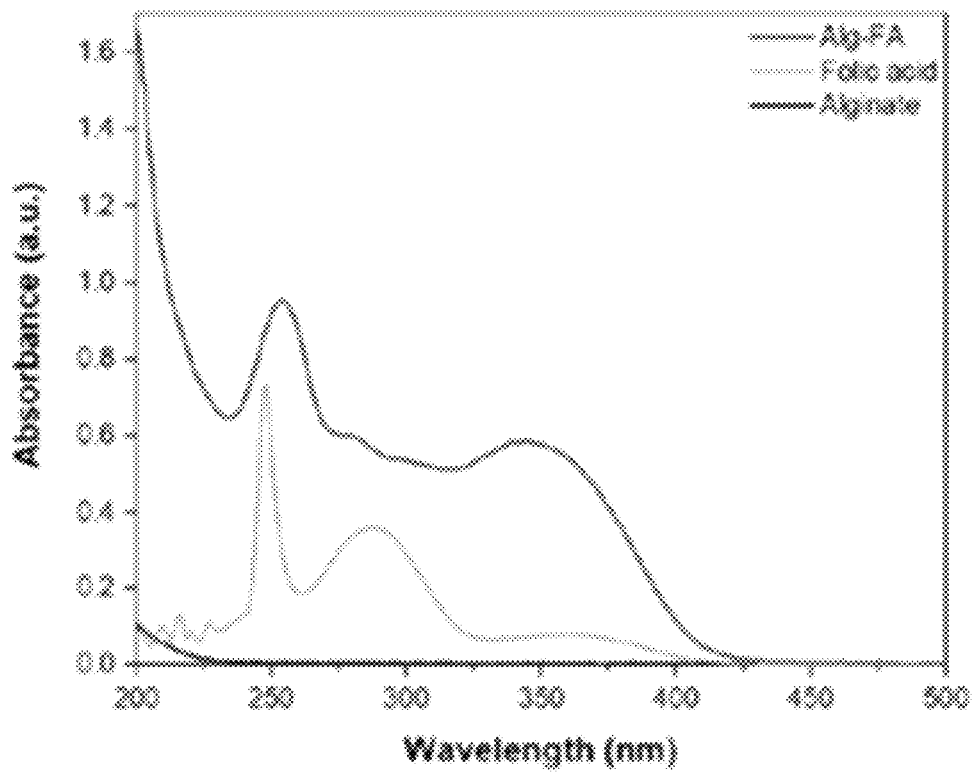

Experimental Example 1. Physicochemical Characterization of Alginic Acid-Folic Acid Conjugate and Nanocarriers Containing the Same The structures of AF and NPs were analyzed by $^1$H NMR (proton nuclear magnetic resonance), FT-IR (Fourier transform infrared) and UV-vis. $^1$H NMR spectra (JNM-LA400, JEOL, Japan) were measured at 400 MHz; alginic acid and AF were measured at 80° C. and other compounds were measured at 25° C. (see FIG. 2). FT-IR spectra (ALPHA, Bruker, USA) were analyzed at a frequency range of 4,000 to 400 $cm^{-1}$ to characterize AF (see FIG. 2A). UV-vis spectral analysis was performed using a Nanodrop 2000 spectrophotometer (Thermo Fisher, USA) (see FIG. 2B).

Figure 4A:
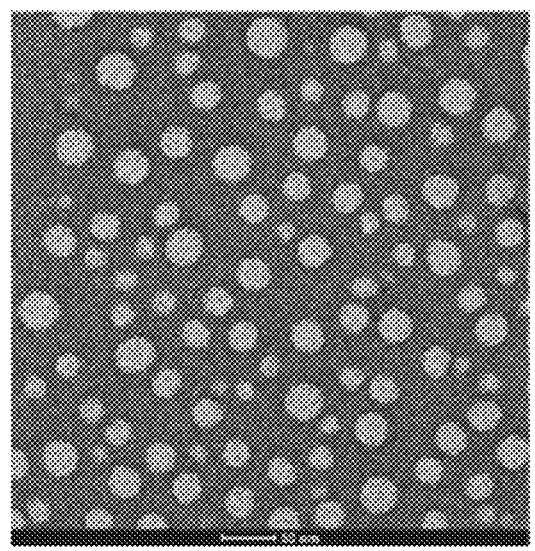
FIGS. 4A and 4B show the results of analyzing the physiochemical characteristics of the alginic acid-folic acid conjugate according to one embodiment of the present invention, and depicts a TEM image showing the morphology of NP4 (FIG. 4A), and a size distribution obtained by measuring the diameters of 230 NPs (FIG. 4B).
Figure 4B:
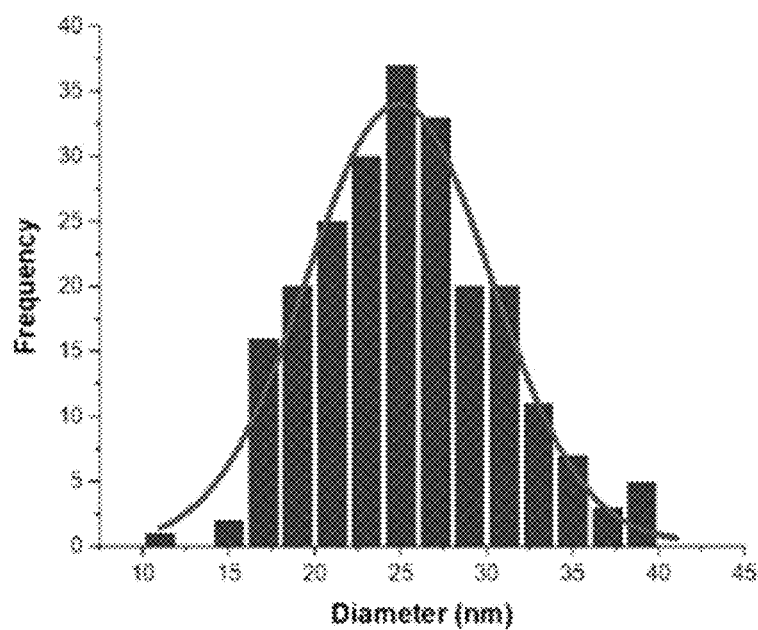
Figure 5:
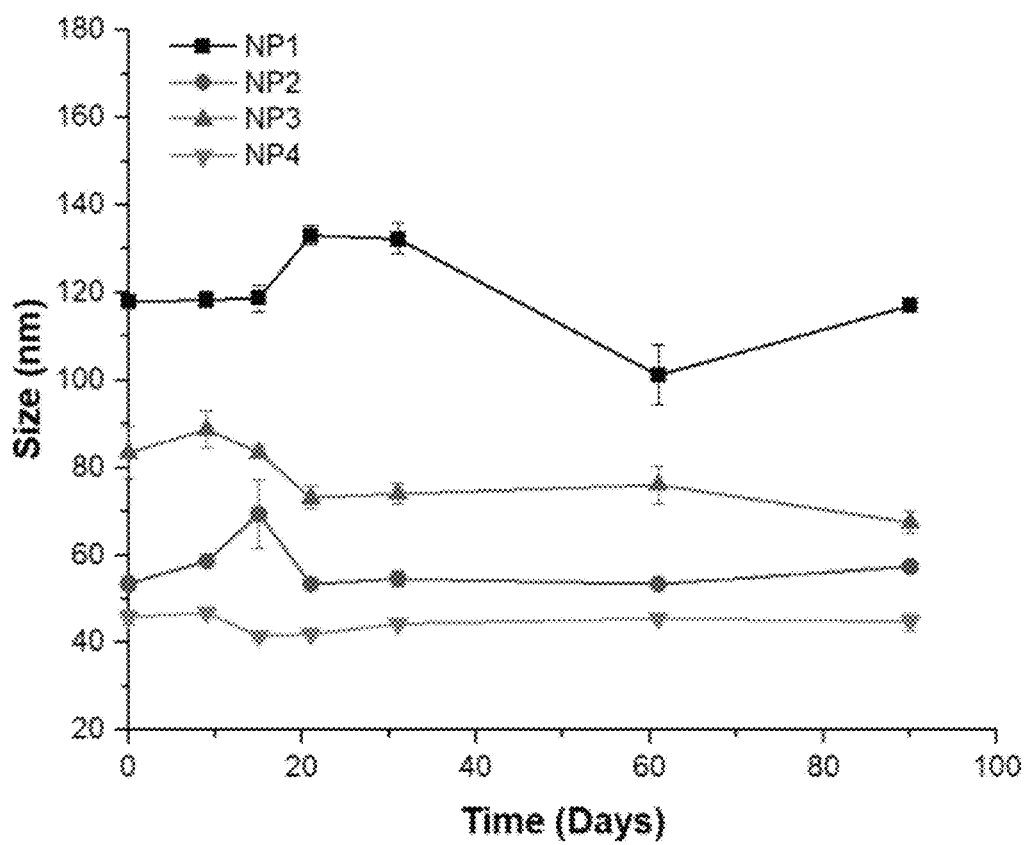
FIG. 5 shows the results of analyzing the physiochemical characteristics of the alginic acid-folic acid conjugate according to one embodiment of the present invention, and is a graph showing the stability of NP1 to NP4 over time.

As a result, as shown in FIG. 4, it was confirmed that the NPs had spherical morphology and were monodispersed without aggregation, and the average particle size of 230 NPs was about 25 nm. In addition, as shown in FIG. 5, it was confirmed that the NPs were stably maintained without a significant change in the size distribution for 3 months.

In addition, the average size, zeta (0 potential, 5-ALA loading capacity (LC) and encapsulation efficiency (EE) of the NPs were measured using a Zetasizer (Malvern, UK).

The average size of the NPs was measured using dynamic light scattering (DLS) at 25° C. at an angle of 173°.

To measure the concentration of 5-ALA contained in the NPs, NPs (1 mL) were dispersed in 1.5% hydrogen peroxide (1.5 mL) and sonicated in an ultrasonic water bath for 10 min at 37° C., and then stirred vigorously for 2 hours. Next, the NP decomposition product was centrifuged at 12,300×g using a Microsep device (MWCO 1 kDa), and the supernatant containing 5-ALA was collected and lyophilized under reduced pressure. Thereafter, 5-ALA was quantified using TNBSA (2,4,6-trinitrobenzene sulfonic acid) (5% w/v) (Thermo Fisher, USA) according to the manufacturer's instructions. The 5-ALA loading capacity (LC) and encapsulation efficiency (EE) were calculated according to the following equations:

$$LC\ (\%) = \text{5-ALA content in nanocarrier/nanocarrier weight} \times 100$$

$$EE\ (\%) = \text{5-ALA content in nanocarrier/total 5-ALA content} \times 100 \quad \text{[Equation 1]}$$

As a result, as shown in Table 1 below, it was confirmed that NP4 was the smallest in size and the average particle size thereof was about 45 nm, which could efficiently penetrate cancer cells. Zeta potential is an indicator of the stability of the nanoparticles, and it was confirmed that all NPs had a negative average surface charge due to the carboxyl group of the alginic acid, suggesting that the NPs were stably formed in a suspended state. The 5-ALA loading capacity increased with increasing AF concentration, and the encapsulation efficiency was the highest at an AF concentration of 1 wt %. This was believed to be due to an increase in the number of ionic bonds between alginic acid and 5-ALA with amphoteric ions. Therefore, as the AF concentration increased, a higher concentration of 5-ALA was encapsulated, and thus the encapsulation efficiency also increased. Based on these results, in the subsequent experiment, 5-ALA release profile assessment, cytotoxicity assessment and PpIX quantification were performed using NP4.

TABLE 1

| NP | Alginic acid-folic acid (wt %) | HLB | Day 0 Size (nm) | PDI | Zeta potential (mV) | LC % | EE % |
|---|---|---|---|---|---|---|---|
| NP1 | 0.5 | 7 | 117.9 ± 0.65 | 0.389 | −27.4 ± 2.1 | 1.2% | 6.33% |
| NP2 | 0.5 | 8 | 53.56 ± 1.52 | 0.496 | −23.3 ± 0.7 | 0.4% | 8.8% |
| NP3 | 1 | 7 | 83.45 ± 3.47 | 0.584 | −22.8 ± 2 | 2.8% | 27.14% |
| NP4 | 1 | 8 | 45.89 ± 1.56 | 0.454 | −29.3 ± 0.1 | 1.8% | 31.6% |

In addition, the characteristics of NP1 to NP4 produced to have different AF concentrations and surfactant mixture proportions were analyzed. The morphology of NPs was observed using transmission electron microscopy (TEM JEM-3010, JEOL, Japan). Furthermore, the stability of NPs was assessed by measuring the size thereof for 3 months during storage at 4° C.

Experimental Example 2. 5-ALA Release Profile of Nanocarrier Containing Alginic Acid-Folic Acid Conjugate The 5-ALA release profile was assessed under two different pH environments (pH 5.0 and pH 7.4) at 37° C. First, NP4 (2 mL) were placed in a dialysis membrane (MWCO 1 kDa) in 8 mL PBS at pH 5.0 or pH 7.4 and stirred at 37° C.

After a fixed time, the release solution was taken out and fresh PBS was added thereto. The concentration of 5-ALA in the dialysis solution was analyzed with a microplate reader (Synergy H1, BioTek, USA) using TNBSA solution according to the manufacturer's instruction. The cumulative 5-ALA concentration released from NPs was calculated according to the following Equation 2:

$$\text{Cumulative release (\%)} = \frac{V_0 C_s + V_r \sum C_{s-1}}{T_{ALA}} \times 100 \quad \text{[Equation 2]}$$

wherein $T_{ALA}$ indicates the total content of 5-ALA in the NPs, $V_0$ indicates the total volume (10 mL) of the release solution, $V_r$ indicates the volume (1 mL) of the added PBS, and $C_s$ indicates the concentration of 5-ALA in the sample.

Figure 6:
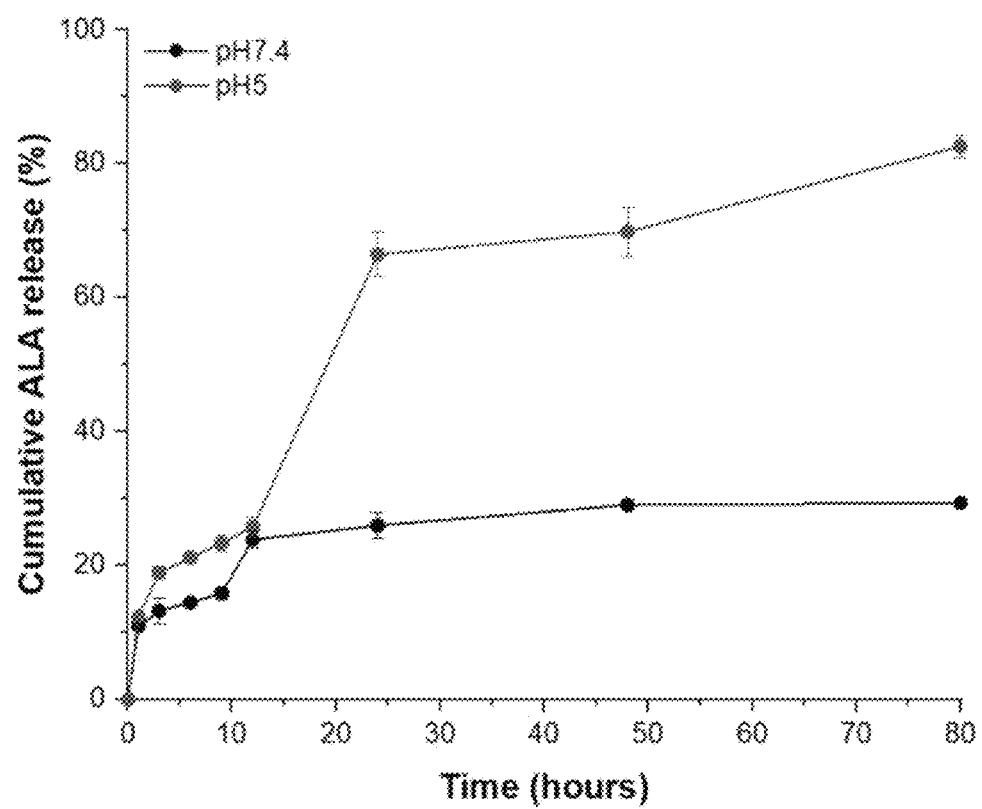
FIG. 6 is a graph showing the intracellular cumulative 5-ALA release (%) of the alginic acid-folic acid conjugate according to one embodiment of the present invention.
Figure 7A:
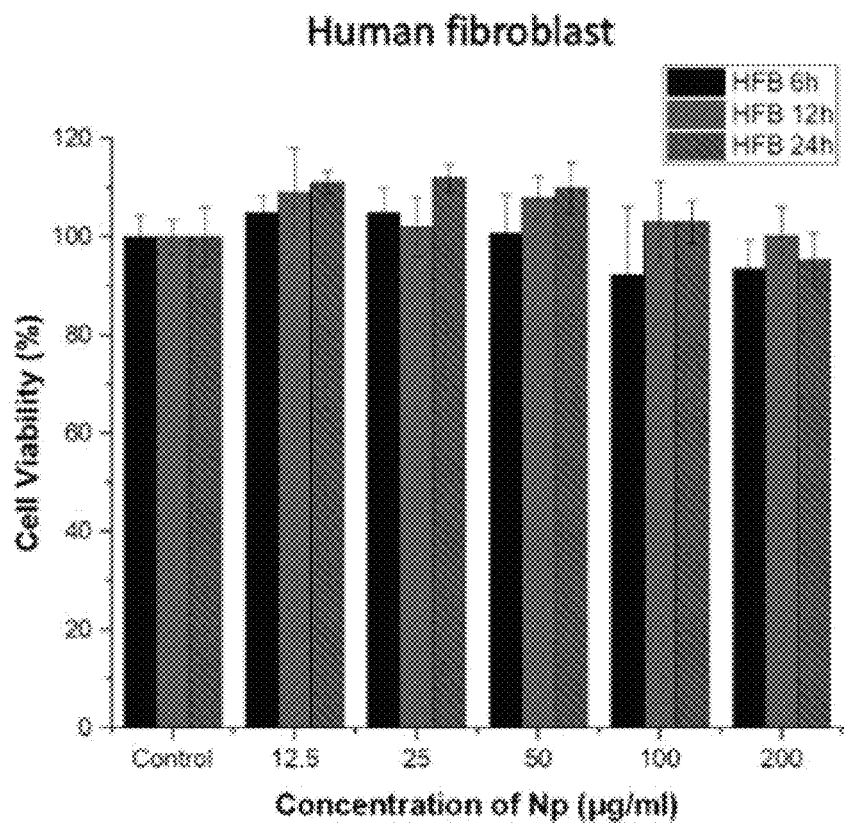
FIGS. 7A, 7B, 7C and 7D show the results of evaluating the cytotoxicity of the alginic acid-folic acid conjugate according to one embodiment of the present invention.
Figure 7B:
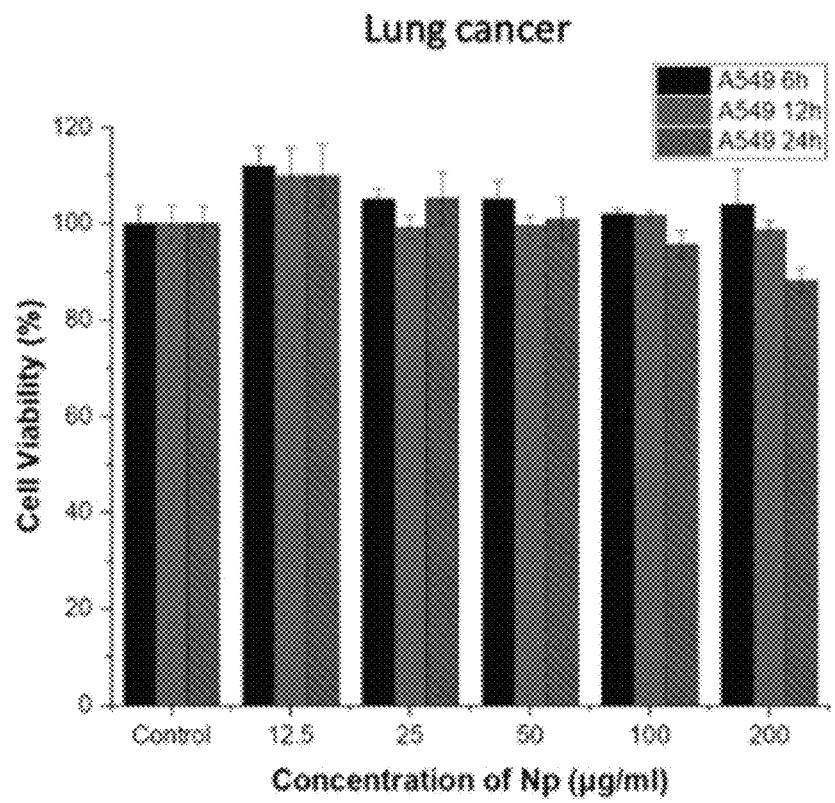
Figure 7C:
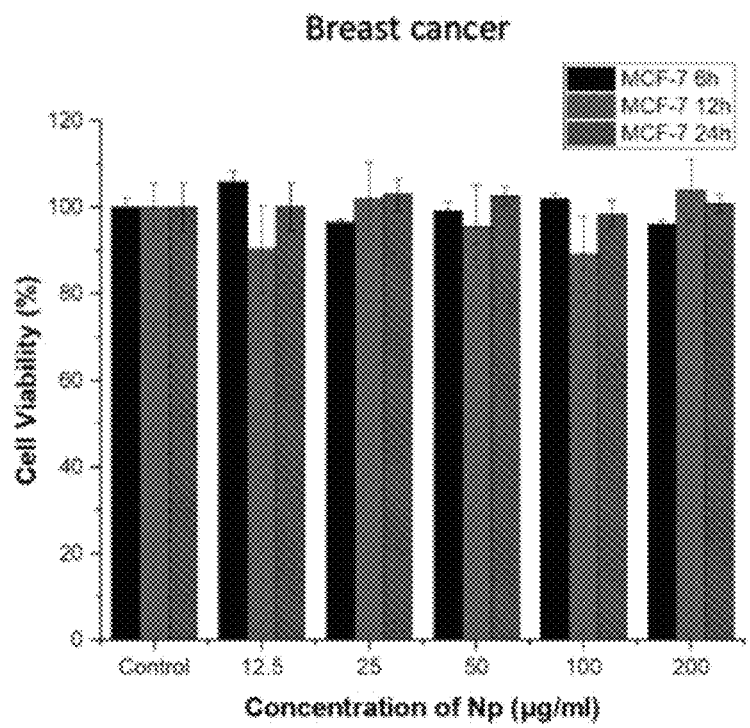
Figure 7D:
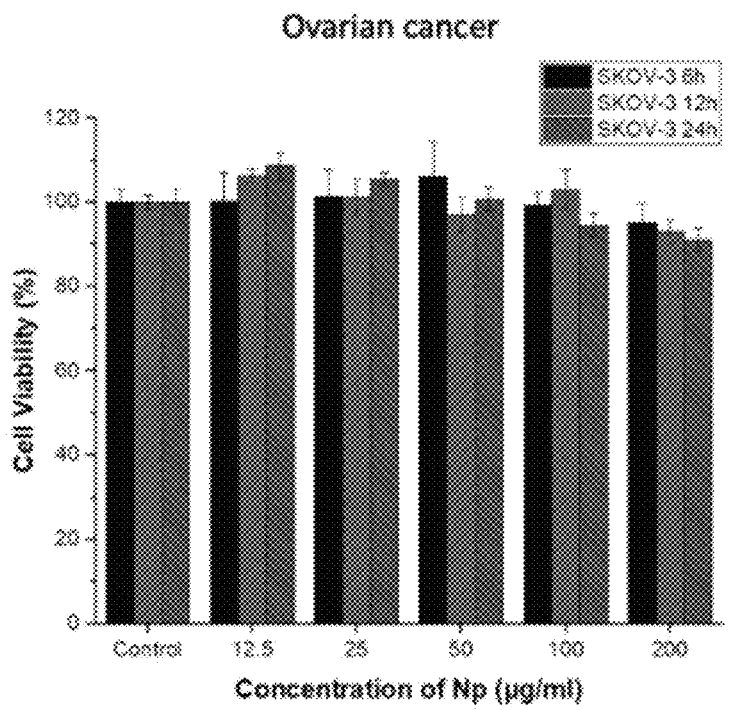

As a result, as shown in FIG. 6, it was confirmed that no more than 30% of 5-ALA was released over the experimental period at pH 7.4, indicating indicate that the 5-ALA contained in NPs remained stable under physiological conditions. However, more than 80% of 5-ALA was released after 80 hours at pH 5, while the 5-ALA was released from 12 to 24 hours. This release was due to the deprotonation and decomposition of the alginic acid carboxyl group at acidic pH. Thus, it can be seen that acid-catalyzed hydrolysis of alginic acid occurs in acidic environments, and NPs are deprotonated to release the drug in the carrier. Thus, these results suggest that a contrast agent containing NPs may be used for imaging gastrointestinal tract cancer.

Experimental Example 3. Measurement of Cytotoxicity of Nanocarrier Containing Alginic Acid-Folic Acid Conjugate The human fibroblast cell line HFB was cultured in Dulbecco's Modified Eagle's Medium (DMEM) containing 10% fetal bovine serum (FBS) and 1% penicillin-streptomycin (PS). MCF-7 (breast adenocarcinoma), A549 (lung cancer) and SKOV-3 (ovarian adenocarcinoma) cell lines were cultured in RPMI 1640 containing 10% FBS and 1% PS. All cell lines were procured from the Korea Cell Line Bank and cultured in a humidified 37° C. constant temperature incubator set to 5% $CO_2$.

For cytotoxicity measurement, the HFB, MCF-7, A549 and SKOV-3 cell lines were used. First, cells were placed in in 96-well plates at a density of $5 \times 10^3$ cells per well and preincubated for 24 hours at 37° C. Then, each well was treated with 12.5, 25, 50, 100 or 200 μg/mL of NP4 and incubated at 37° C. for 6, 12 or 24 hours. After the NP-containing medium was removed, the medium was treated with CCK-8 solution and allowed to react in an incubator at 37° C. for 2 hours. Absorbance was measured at 450 nm using a microplate reader.

Folic acid and 5-ALA are normally present in the body, and alginic acid is also a natural product and is a clinically approved substance. As shown in FIG. 7, it was confirmed that NPs had no cytotoxicity regardless of the concentration and incubation time thereof, suggesting that they had excellent biocompatibility.

Experimental Example 4. Quantification of PpIX by Nanocarrier Containing Alginic Acid-Folic Acid Conjugate To quantify the intracellular accumulation of PpIX, cells were placed in 24-well plates at a density of $0.5 \times 10^6$ cells per well. After 48 hours of culture, the medium was replaced with a fresh FBS-free medium containing NPs (0.1 mg/mL) and further incubated for 24 hours. After intracellular uptake of NPs and conversion of 5-ALA to PpIX, the culture medium containing NPs was removed and cells were washed with PBS. Then, 100 μL of cold RIPA lysis buffer solution was added to each well, mixed well, and incubated on ice for 30 min, followed by vortexing 4 to 6 times. The lysis solution was centrifuged at 14,000×g at 4° C. for 20 minutes. The supernatant was added to a black 96-well plate, and the fluorescence intensity at 635 nm emission wavelength (405 nm excitation wavelength) was measured with a microplate reader. BSA (bicinchoninic acid) (Thermo Fisher, USA) assay was used to obtain a quantitative fluorescence value according to the cell numbers by normalizing the fluorescence intensity to the total protein concentration of the cell lysate.

Figure 8:
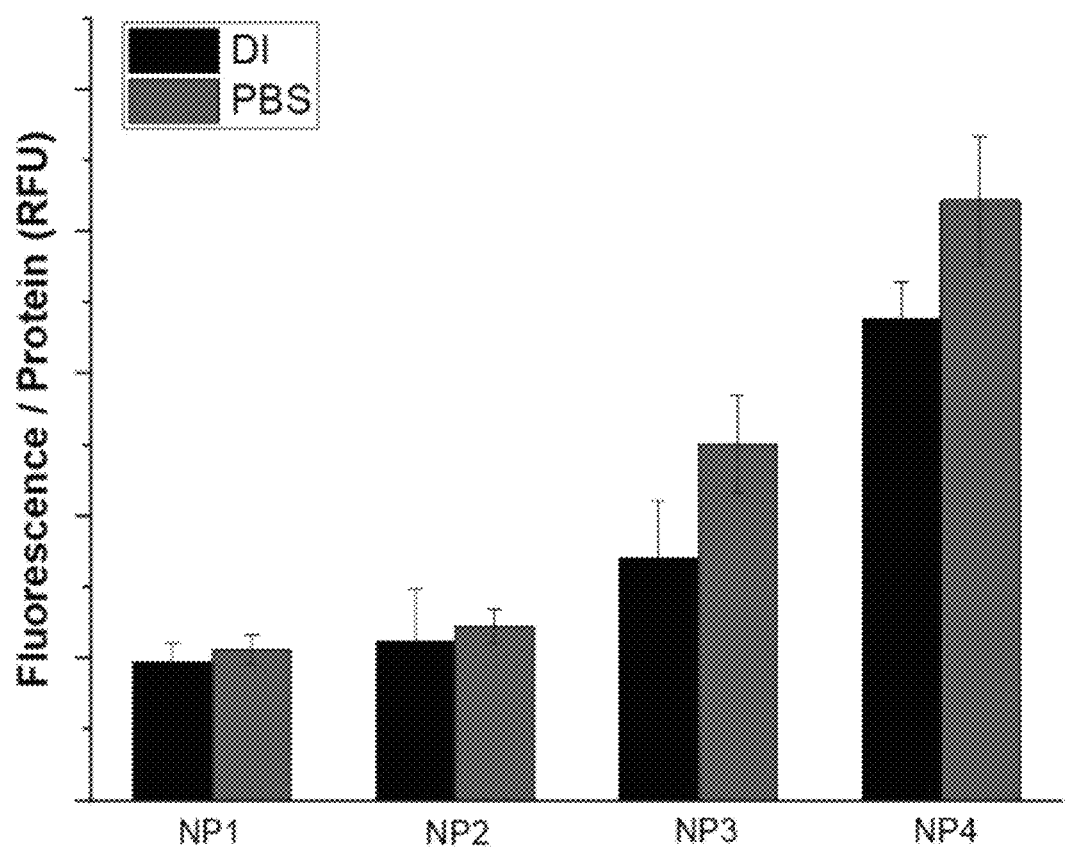
FIG. 8 is a graph showing the results of quantitatively measuring the fluorescence of NP1 to NP4, each including the alginic acid-folic acid conjugate according to one embodiment of the present invention.
Figure 9A:
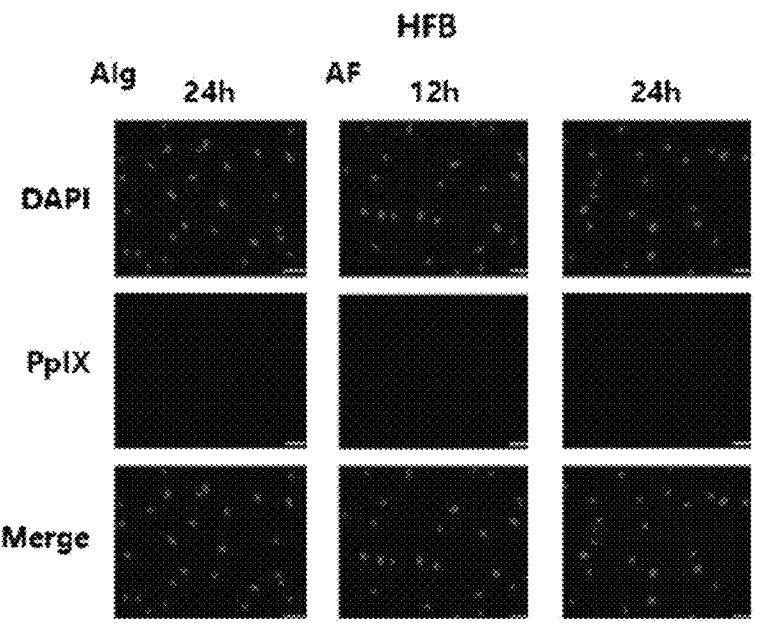
FIGS. 9A, 9B, 9C and 9D depict fluorescence images showing intracellular PpIX production by the alginic acid-folic acid conjugate according to one embodiment of the present invention.
Figure 9B:
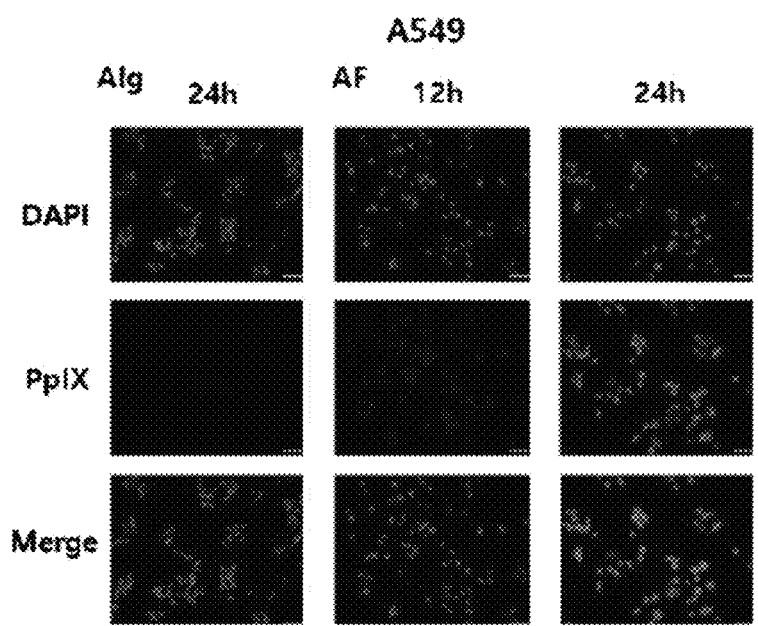
Figure 9C:
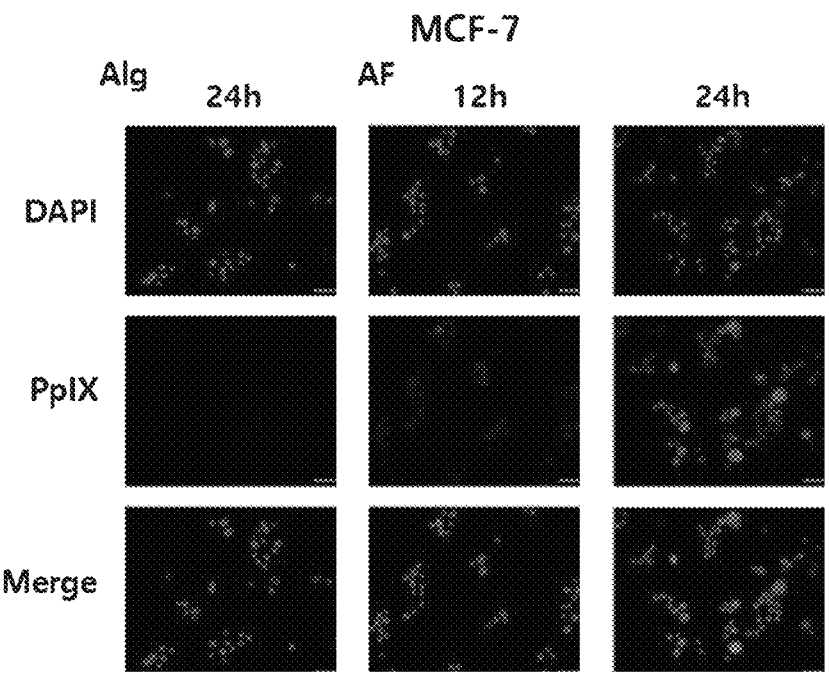
Figure 9D:
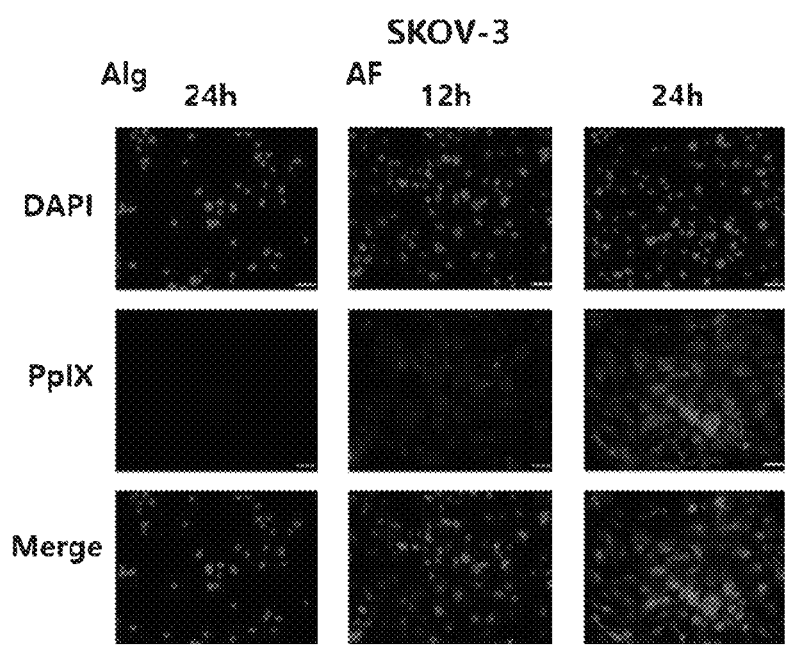

As a result, as shown in FIG. 8, it was confirmed that the fluorescence intensity was higher in the case in which the cancer cells were treated with the four types of NPs dispersed in PBS than the case in which the cells were treated with the NPs dispersed in DI water. In particular, NP4 showed the strongest fluorescence intensity, and was used in a subsequent cellular internalization test.

Experimental Example 5. Measurement of Cellular Internalization of Nanocarrier Containing Alginic Acid-Folic Acid Conjugate To analyze the cellular uptake of NPs, a normal cell line and three cancer cell lines were placed in 48-well plates at a density of $0.05 \times 10^6$ cells per well and preincubated at 37° C. for 48 hours. The medium was replaced with a fresh FBS-free medium containing NP4 (0.1 mg/mL) and incubated for 12 or 24 hours. Then, the cells were washed with PBS and 100 μL of 4% paraformaldehyde solution was added to each well, followed by fixing for 15 min. 4',6-diamidino-2-phenylindole (DAPI) was used for cell nuclei staining and kept at room temperature for 20 min. After staining, the cells were washed using Dulbecco's PBS and fluorescence images were acquired using a confocal fluorescence microscope (Zeiss Z1 Axio Observer, Carl Zeiss, Germany). Fluorescence of PpIX was imaged under the conditions of AT560/40 nm excitation and 635/60 nm emission filters.

Figure 10:
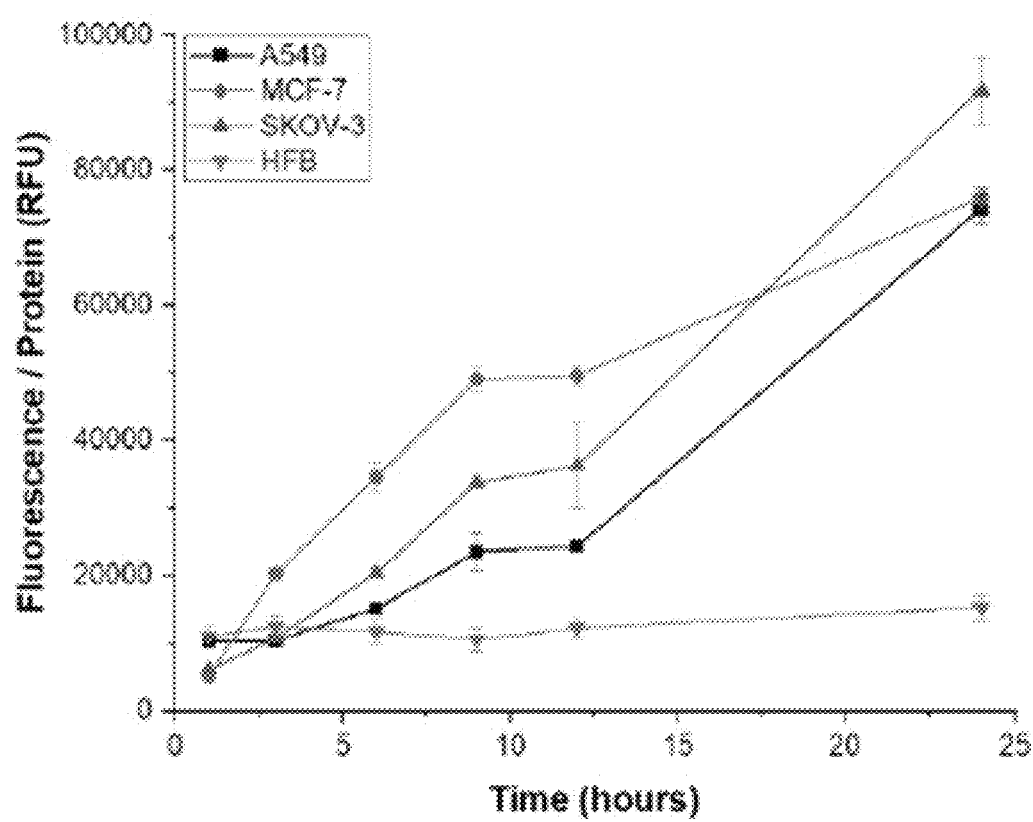
FIG. 10 is a graph showing the results of quantitatively measuring fluorescence corresponding to intracellular PpIX production by the alginic acid-folic acid conjugate according to one embodiment of the present invention.

As a result, as shown in FIGS. 9 and 10, the nanocarrier (Alg) containing alginic acid did not display fluorescence in the cancer cells, whereas the nanocarrier (NP) containing the alginic acid-folic acid conjugate displayed fluorescence. In addition, while no fluorescence was observed in the normal cell line HFB, fluorescence was observed in the three cancer cell lines from 12 hours at which alginic acid started to be degraded after NP uptake. Thus, it could be seen that NPs were selectively uptaken into cancer cells. In addition, it was confirmed that the fluorescence intensity gradually increased up to 12 hours in cancer cells and rapidly increased up to 24 hours. The fluorescence intensities of the A549 and MCF-7 cell lines were similar up to 24 hours, and the SKOV3 cell line showed stronger fluorescence intensity than the MCF7 and A549 cell lines.

So far, the present invention has been described with reference to preferred embodiments. Those of ordinary skill in the art to which the present invention pertains will appreciate that the present invention may be embodied in modified forms without departing from the essential characteristics of the present invention. Therefore, the disclosed embodiments should be considered from an illustrative point of view, not from a restrictive point of view. The scope of the present invention is defined by the claims rather than the foregoing description, and all differences within the scope equivalent thereto should be construed as being included in the present invention.

We claim:

1. An alginic acid-folic acid conjugate in which a carboxyl group of folic acid is linked to a hydroxyl group of alginic acid via an ester bond, or a pharmaceutically acceptable salt thereof, wherein the alginic acid-folic acid conjugate is represented by the following Formula 1:

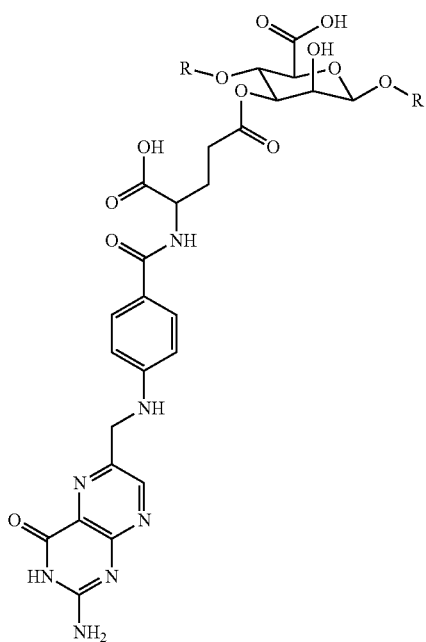

[Formula 1]

wherein R is an alginic acid unit or an alginic acid polymer.

2. The alginic acid-folic acid conjugate or pharmaceutically acceptable salt thereof according to claim 1, wherein an amine group bound to a dihydropteridine moiety remains unreacted.

3. The alginic acid-folic acid conjugate or pharmaceutically acceptable salt thereof according to claim 1, wherein the salt of the alginic acid-folic acid conjugate is represented by the following Formula 1-1:

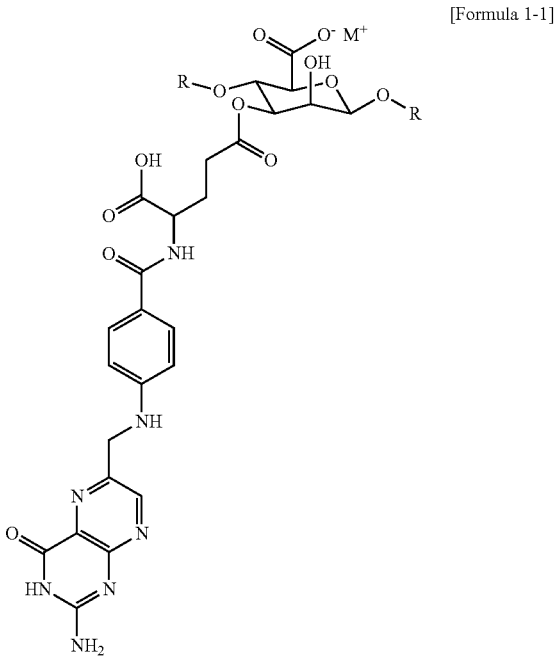

[Formula 1-1]

wherein R is an alginic acid unit or an alginic acid polymer, and M is Na, K, Mg, Ca, or Ba.

4. A pharmaceutical composition for diagnosing cancer containing the alginic acid-folic acid conjugate or pharmaceutically acceptable salt thereof according to claim 1.

5. The pharmaceutical composition of claim 4, further containing a fluorescence inducing substance.

6. A method for producing an alginic acid-folic acid conjugate comprising steps of:
   a) introducing a protecting group to a carboxyl group of alginic acid;
   b) introducing a leaving group to a carboxyl group of folic acid; and
   c) obtaining a reaction product between the alginic acid to which the protecting group has been introduced in step a) and the folic acid to which the leaving group has been introduced in step b), wherein the protecting group in step a) is an unsubstituted or substituted benzyl group, trimethylsilyl, t-butyldimethylsilyl, t-butyldiphenylsilyl, a substituted or unsubstituted alkyl group having 1 to 4 carbon atoms, or tetrabutylammonium, and wherein the leaving group in step b) is a methanesulfonyl group, a p-toluenesulfonyl group, a trifluoromethanesulfonyl group, an alkoxy group having 1 to 5 carbon atoms, a halogen or imidazole.

7. The method of claim 6, wherein the protecting group in step a) is tetrabutylammonium.

8. The method of claim 6, wherein the leaving group in step b) is imidazole.

9. The method of claim 6, wherein the reaction product obtained in step c) is one in which a hydroxyl group of alginic acid and the carboxyl group of folic acid are bonded to each other via an ester bond.

10. The method of claim 6, wherein step a) comprises producing the alginic acid from alginic acid salt and introducing the protecting group to the carboxyl group of the alginic acid at a pH of 8 to 10.

* * * * *